(12) United States Patent
Tsuji

(10) Patent No.: US 7,160,835 B2
(45) Date of Patent: Jan. 9, 2007

(54) BISPHOSPHINE PROCESS FOR PRODUCING THE SAME AND USE THEREOF

(75) Inventor: Tomoaki Tsuji, Okayama (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 10/506,676

(22) PCT Filed: Jan. 10, 2003

(86) PCT No.: PCT/JP03/00153

§ 371 (c)(1),
(2), (4) Date: Sep. 17, 2004

(87) PCT Pub. No.: WO03/080632

PCT Pub. Date: Oct. 2, 2003

(65) Prior Publication Data

US 2005/0164874 A1     Jul. 28, 2005

(30) Foreign Application Priority Data

Mar. 22, 2002   (JP)   ............................. 2002-080629

(51) Int. Cl.
  *B01J 31/00*   (2006.01)
  *C07F 9/02*   (2006.01)
(52) U.S. Cl. ...................... 502/162; 502/150; 502/152; 502/155; 502/104; 568/13
(58) Field of Classification Search ................ 502/162, 502/150, 152, 155, 104; 568/13
See application file for complete search history.

(56) References Cited

U.S. PATENT DOCUMENTS

| | | | | |
|---|---|---|---|---|
| 3,532,772 | A * | 10/1970 | Mare et al. | 525/267 |
| 4,694,109 | A | 9/1987 | Devon et al. | |
| 4,960,949 | A * | 10/1990 | Devon et al. | 568/454 |
| 5,520,722 | A * | 5/1996 | Hershkowitz et al. | 95/159 |
| 5,675,041 | A * | 10/1997 | Kiss et al. | 568/454 |
| 5,922,634 | A * | 7/1999 | Bahrmann et al. | 502/166 |
| 6,570,033 | B1 * | 5/2003 | Rottger et al. | 558/78 |
| 6,639,114 | B1 * | 10/2003 | Ahlers et al. | 568/444 |
| 6,818,770 | B1 * | 11/2004 | Selent et al. | 546/25 |

OTHER PUBLICATIONS

Kapoor, Pramesh N., Transition Metal Complexes of the Trans-spanning ditertiary phosphine, bis {3- [bis(3-trifluoromethylphenyl)- phosphinomethyl] phenyl} ether, Journal of Organometallic Chemistry, vol. 341, No. 1-3, pp. 363-366 1988.

Kapoor, Pramesh N., Nickel(II), Palladium(II) and Platinum(II) Complexes of Trans-Spanning Ditertiary Phosphine 3,3'-oxybis [(di-meta-tolylphosphino)methyl]benzene. Journal of Organometallic Chemistry, vol. 315, No. 3, pp. 383-386 1986.

Baltensperger, Urs et al., Multistep Cyclometalation of Solid trans-Dichloro [3,3'-oxybis[((diphenylphosphino)methyl)-benzene]]platinum(II), Organometallics. vol. 2, No. 5 pp. 571-578 1983.

Kranenburg, Mirko et al. "New Diphosphine Ligands Based on Heterocyclic Aromatics Inducing Very High Regioselectivity in Rhodium-Catalyzed Hydroformylation: Effect of the Bite Angle", Organometallics, vol. 14, pp. 3081-3089 1995.

Casey, Charles P. et al. "Diphosphines with Natural Bite Angle near 120° Increase Selectivity for n-Aldehyde Formation in Rhodium-Catalyzed Hydroformylation", J. Am. Chem. Soc. vol. 114, pp. 5535-5543 1992.

* cited by examiner

Primary Examiner—J. A. Lorengo
Assistant Examiner—Jennine Brown
(74) Attorney, Agent, or Firm—Oblon, Spivak, McClelland, Maier & Neustadt, P.C.

(57) ABSTRACT

Bisphosphines represented by the general formula (I)

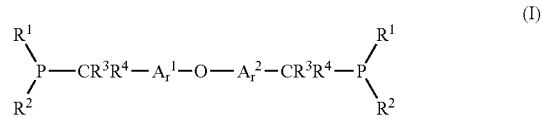

wherein $Ar^1$ and $Ar^2$ each represents an arylene group which may be substituted; $R^1$ and $R^2$ each represents an alkyl group which may be substituted, or an aryl group which may be substituted, or $R^1$ and $R^2$ may combinedly form a ring together with the phosphorus atom bonded thereto; $R^3$ and $R^4$ each represents hydrogen atom or an alkyl group; and the carbon atoms each having $R^3$ and $R^4$ are bonded in positions ortho to the oxygen atom bonded to $Ar^1$ and $Ar^2$; process for production thereof; Group VIII metal complexes comprising said bisphosphines; and process for producing aldehydes, which comprises, on hydroformylation of ethylenically unsaturated compounds with carbon monoxide and hydrogen, using said Group VIII metal complexes.

The hydroformylation of ethylenically unsaturated compounds according to the present invention can produce n-aldehydes at higher reaction rate and industrially more advantageously than with catalysts comprising conventional phosphines, while suppressing side re-actions such as hydrogenation and isomerization.

22 Claims, No Drawings

BISPHOSPHINE PROCESS FOR PRODUCING THE SAME AND USE THEREOF

TECHNICAL FIELD

The present invention relates to novel bisphosphines, processes for producing the same, and uses thereof.

The bisphospines provided by the present invention are useful as components of the hydroformylation catalysts which are used on hydroformylation of ethylenically unsaturated compounds with carbon monoxide and hydrogen to obtain the corresponding aldehydes. Accordingly, the above uses include Group VIII metal complexes that can act as hydroformylation catalysts and are obtainable by complex formation of the bisphosphines of the present invention and Group VIII metal compounds, and also processes for producing aldehydes which comprises using the Group VIII metal complex catalysts as hydroformylation catalysts. On performing hydroformylation of ethylenically unsaturated compounds with carbon monoxide and hydrogen, use of such Group VIII metal complexes can produce the corresponding n-aldehydes at high reaction rate and with good selectivity, while suppressing side reactions such as hydrogenation and isomerization.

BACKGROUND ART

Reaction of ethylenically unsaturated compounds with hydrogen and carbon monoxide in the presence of a Group VIII metal compound or metal complex comprising such a Group VIII metal compound and a phosphorous compound, to produce the corresponding aldehydes is known as hydroformylation or oxo reaction. Production of aldedhydes by this reaction has been of high commercial value.

For the hydroformylation, rhodium complexes comprising rhodium and a phosphorous compound are used as catalysts commercially. It is known that, with hydroformylation, the reaction rate and the selectivity to a linear aldehyde (hereinafter referred to as "n-aldehyde") or a branched aldehyde (hereinafter referred to as "iso-aldehyde") depend significantly on the structure of the phosphorous compound constituting the catalyst used.

As the phosphorous compound, triphenylphospine, which is a monophosphine, is generally used commercially. In this case, the selectivity to n-aldehydes is low. In order to increase the selectivity to n-aldehydes, use of bisphosphines comprising two diphenylphosphines crosslinked together via a specific divalent organic group (hereinafter this group is referred to as "crosslinking group") has been proposed.

For example, (1) it has been reported that with hydroformylation of propylene with use of 2,2'-bis(diphenylphosphinomethyl)biphenyl (hereinafter referred to as "BISBI") the ratio of selectivities to n-aldehyde and iso-aldehyde (hereinafter referred to as "n/iso ratio") is 25.1/1, which is markedly higher than 2.43/1, which is the case with triphenylphosphine which is a monophosphine (see U.S. Pat. No. 4,694,109); and (2) it is known that with hydroformylation of 1-octene with use of 9,9-dimethyl-4,6-bis(diphenylphosphino)xanthene (hereinafter referred to as "Xantphos") the n/iso ratio is 53.5 [see Organometallics, 14, 6, 3081–3089 (1995)].

According to the knowledge of the present inventor, although hydroformylation of 7-octen-1-al with the above BISBI or Xantphos can surely yield the corresponding n-aldehyde with higher selectivity than the reaction with triphenylphosphine, this reaction is not satisfactory due to low catalytic activity and, further, has problems that side reactions such as hydrogenation and isomerization occur.

With respect to the relationship between the structure of the bisphosphine used and the resulting n/iso ratio, it has been reported that, with a metal complex comprising a Group VIII metal compound and a bisphosphine, the closer to 120° the angle formed by phosphorus-rhodium-phosphorus is, the higher the n/iso ratio is [see Journal of the American Chemical Society, 114, 14, 5535–5543(1992) and Organometallics, 14, 6, 3081–3089(1995)]. However, the above literature report nothing about the relationship between the structure of the bisphosphine used and the selectivity to side reactions such as hydrogenation and isomerization.

Accordingly, an object of the present invention is to provide a bisphosphine constituting a hydroformylation catalyst that can, on hydroformylation of ethylenically unsaturated compounds, exert high catalytic activity and yield n-aldehydes with high selectivity while suppressing side reactions such as hydrogenation and isomerization.

Another object of the present invention is to provide a process for producing the above bisphosphine.

Still another object of the present invention is to provide a Group VIII metal complex that can act as a hydroformylation catalyst, said complex comprising the above bisphosphine and a Group VIII metal compound.

Yet another object of the present invention is to provide a process for producing aldehydes which comprises effecting hydroformylation of an ethylenically unsaturated compound with carbon monoxide and hydrogen with use of the above Group VIII metal complex.

DISCLOSURE OF THE INVENTION

The present invention provides a bisphosphine having a crosslinking group and represented by the general formula (I) (hereinafter referred to as "bisphosphine (I)")

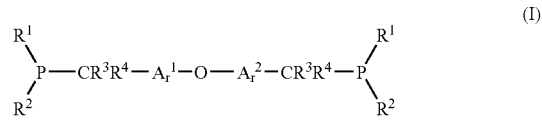

wherein $Ar^1$ and $Ar^2$ each represents an arylene group which may be substituted; $R^1$ and $R^2$ each represents an alkyl group which may be substituted or an aryl group which may be substituted, or $R^1$ and $R^2$ may combinedly form a ring together with the phosphorus atom bonded thereto; $R^3$ and $R^4$ each represents hydrogen atom or an alkyl group; and the carbon atoms each having $R^3$ and $R^4$ are bonded in positions ortho to the oxygen atom bonded to $Ar^1$ and $Ar^2$.

The present invention also provides a process for producing bisphosphine (I), which comprises subjecting a compound represented by the general formula (II) (hereinafter referred to as "compound (II))

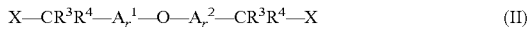

wherein $Ar^1$, $Ar^2$, $R^3$ and $R^4$ are as defined above, and X represents an arylsulfonyloxy group, alkylsulfonyloxy group or a halogen atom;

to phosphorylation with an alkali metal phosphide represented by the general formula (III) (hereinafter referred to as "alkali metal phosphide (III)")

(III)

wherein R¹ and R² are as defined above, M represents lithium atom, sodium atom or potassium atom.

The present invention further provides a Group VIII metal complex comprising a Group VIII metal compound and a bisphosphine (I) (hereinafter referred to as "Group VIII metal complex (A)").

The present invention still further provides a process for producing aldehydes, which comprises, on hydroformylation of an ethylenically unsaturated compound with carbon monoxide and hydrogen in the presence of a catalyst to produce the corresponding aldehyde, using as the catalyst the Group VIII metal complex (A).

MODES FOR CARRYING OUT THE INVENTION

Preferred examples of the arylene groups represented by Ar¹ and Ar² are those having 6 to 20 carbon atoms. Concrete examples include phenylene, naphthylene and anthrathylene, 1,1'-biphenylene and 1,1'-binaphthylene. These arylene groups may be substituted. Examples of the substituents are halogen atoms, e.g. fluorine atom, chlorine atom and bromine atom; alkyl groups having 1 to 6 carbon atoms, e.g. methyl, ethyl, propyl, isopropyl, butyl, isobutyl, s-butyl, t-butyl and cyclohexyl; fluoroalkyl groups having 1 to 3 carbon atoms, e.g. difluoromethyl, trifluoromethyl, 1,1-difluoroethyl, 2,2-difluoroethyl and 1-fluoropropyl; alkoxy groups having 1 to 4 carbon atoms, e.g. methoxy, ethoxy, propoxy, isopropoxy, butoxy, isobutoxy, s-butoxy and t-butoxy; acyl groups having 2 to 4 carbon atoms, e.g. acetyl, propionyl, butyryl and isobutyryl; acyloxy groups having 2 to 4 carbon atoms, e.g. acetyloxy, propionyloxy, butyryloxy and isobutyryloxy; alkoxycarbonyl groups having 2 to 5 carbon atoms, e.g. methoxycarbonyl, ethoxycarbonyl, propoxycarbonyl, isopropoxycarbonyl, butoxycarbonyl, isobutoxycarbonyl, s-butoxycarbonyl and t-butoxycarbonyl; and carboxylic acid groups (hydroxycarbonyl groups) and salts thereof.

Preferred examples of the alkyl groups which may be represented by R¹ or R² are those having 1 to 6 carbon atoms. Concrete examples include methyl, ethyl, propyl, isopropyl, butyl, isobutyl, s-butyl, t-butyl and cyclohexyl. These alkyl groups may be substituted. Examples of the substituents are halogen atoms, e.g. fluorine atom, chlorine atom and bromine atom; alkoxy groups having 1 to 4 carbon atoms, e.g. methoxy, ethoxy, propoxy, isopropoxy, butoxy, isobutoxy, s-butoxy and t-butoxy; acyl groups having 2 to 4 carbon atoms, e.g. acetyl, propionyl, butyryl and isobutyryl; acyloxy groups having 2 to 4 carbon atoms, e.g. acetyloxy, propionyloxy, butyryloxy and isobutyryloxy; alkoxycarbonyl groups having 2 to 5 carbon atoms, e.g. methoxycarbonyl, ethoxycarbonyl, propoxycarbonyl, isopropoxycarbonyl, butoxycarbonyl, isobutoxycarbonyl, s-butoxycarbonyl and t-butoxycarbonyl; carboxylic acid groups and salts thereof; and sulfonic acid groups and salts thereof.

Preferred examples of the aryl groups which may be represented by R¹ or R² are those having 6 to 14 carbon atoms. Concrete examples are phenyl, naphthyl and anthryl. These aryl groups may be substituted. Examples of the substituents are halogen atoms, e.g. fluorine atom, chlorine atom and bromine atom; alkyl groups having 1 to 6 carbon atoms, e.g. methyl, ethyl, propyl, isopropyl, butyl, isobutyl, s-butyl, t-butyl and cyclohexyl; fluoroalkyl groups having 1 to 3 carbon atoms, e.g. difluoromethyl, trifluoromethyl, 1,1-difluoroethyl, 2,2-difluoroethyl and 1-fluoropropyl; alkoxy groups having 1 to 4 carbon atoms, e.g. methoxy, ethoxy, propoxy, isopropoxy, butoxy, isobutoxy, s-butoxy and t-butoxy; acyl groups having 2 to 4 carbon atoms, e.g. acetyl, propionyl, butyryl and isobutyryl; acyloxy groups having 2 to 4 carbon atoms, e.g. acetyloxy, propionyloxy, butyryloxy and isobutyryloxy; alkoxycarbonyl groups having 2 to 5 carbon atoms, e.g. methoxycarbonyl, ethoxycarbonyl, propoxycarbonyl, isopropoxycarbonyl, butoxycarbonyl, isobutoxycarbonyl, s-butoxycarbonyl and t-butoxycarbonyl; carboxylic acid groups and salts thereof; and sulfonic acid groups and salts thereof.

R¹ and R² may combinedly form a ring together with the phosphorus atom bonded thereto. Examples of such phosphorus-containing heterocyclic ring are 2,5-dimethylphospholane, 2,5-diethylphospholane, 2,5-dipropylphospholane, 2,5-diisopropylphospholane, 5H-Benzo[b]phosphindole, 5,10-dihydro-acryidophosphine, 10H-Phenoxaphosphine, and 10-Phenothiaphosphine. Preferred examples of the alkyl groups which may be represented by R³ or R⁴ are those having 1 to 4 carbon atoms, such as methyl, ethyl, propyl, isopropyl, butyl and isobutyl.

The bisphosphines (I) are novel compounds that have not been described in the literature. The Group VIII metal complexes (A) comprising a component of bisphosphine (I) realize, as described later herein, excellent reaction results when used as hydroformylation catalysts. Preferred bisphosphines (I) are those with, in the general formula (I), Ar¹ and Ar² each representing phenylene, R¹ and R² each representing phenyl, and R³ and R⁴ each representing hydrogen. Representative examples of such bisphosphines (I) are 2,2'-bis(diphenylphosphinomethyl)diphenyl ether, 2,2'-bis(diphenylphosphinomethyl)-6-methoxy-diphenyl ether and 2,2'-bis(diphenylphosphinomethyl)-4-t-butyl diphenyl ether.

The process for producing bisphosphines (I) is now described.

The phosphorilation of a compound (II) with an alkali metal phosphide (III) is desirably carried out in the presence of a solvent. Examples of preferred solvents are ethers, e.g. 1,4-dioxane, dibutyl ether, 2-ethoxyethyl ether, diethyleneglycol dimethyl ether, tetrahydrofuran and diethyl ether. Of these, a mixed solvent comprising tetrahydrofuran and dibutyl ether is suitable for use in the preparation of an alkali metal phosphide (III) and further particularly desirable, since it can facilitate ready separation of the resulting bisphosphine (I) from the alkali metal phosphide (III). The amount of the solvent used is not particularly limited, but it is desirably in a range of 1 to 1000 parts by weight based on the weight of the alkali metal phosphide (III), more preferably in a range of 10 to 100 parts by weight on the same basis, which insures high volume efficiency on separation of the bisphosphine (I) from the reaction mixture.

The above reaction is carried out by adding an alkali metal phosphide (III) dropwise into a solution containing a compound (II) or by adding dropwise a compound (II) into a solution containing an alkali metal phosphide (III).

The amount of the alkali metal phosphide (III) used is desirably in a range of 2 to 4 moles, more preferably in a range of 2 to 2.2 moles, per mole of the compound (II), in view of easy separation of the resulting bisphosphine (I) from the unreacted alkali metal phosphide (III). The reaction temperature is desirably in a range of −75° C. to the reflux temperature of the solvent, more preferably in a range of −75° C. to room temperature, since this range can suppress production of byproducts. The reaction time is desirably in a range of 0.5 to 10 hours, more preferably in a range of 0.5 to 3 hours, which can suppress production of byproducts.

After completion of the reaction, to the reaction mixture containing the bisphosphine (I) as it is or, after the reaction mixture has been condensed, to the condensate, a solvent suitable for water extraction such as toluene, pentane, hexane, diethyl ether, dipropyl ether, butyl methyl ether, tetrahydrofuran, methyl acetate, ethyl acetate or propyl acetate is added. The solution is then washed with water, to separate an organic layer. The bisphosphine (I) can be isolated and purified by recrystallization or like processes from the organic layer.

The compounds (II) are roughly classified into sulfonic acid esters with X in the general formula (II) represents an arylsulfonyloxy or alkylsulfonyloxy group (hereinafter referred to as "sulfonic acid esters (II-a)") and halides with X in the general formula (II) represents a halogen atom (hereinafter referred to as "halides (II-b)").

The sulfonic acid esters (II-a) can be produced by any known process. For example, 2,2'-bis(p-tolyl-sulfonyloxymethyl)-di(substituted)phenyl ether (hereinafter referred to as "sulfonic acid ester (II-a')"), which belongs to the category of sulfonic acid esters (II-a), can be produced as follows.

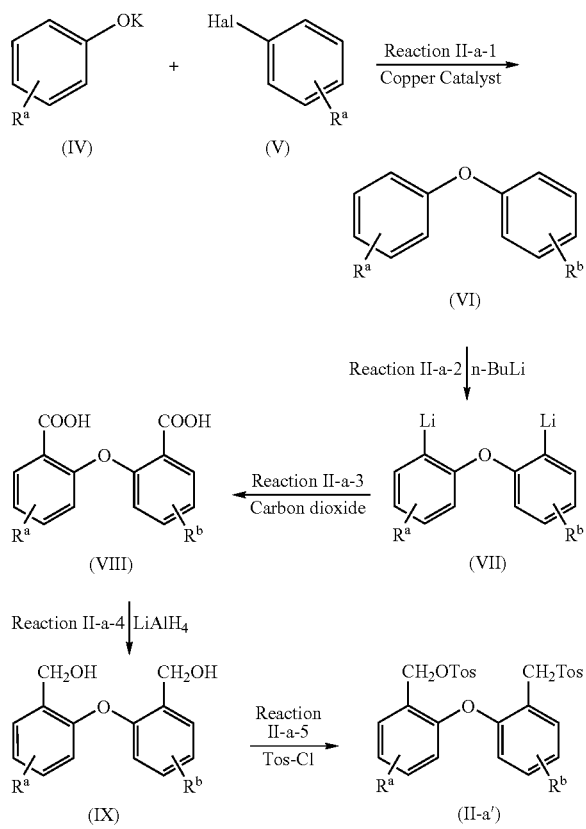

In the above formulas, $R^a$ and $R^b$ each represents a substituent on the benzene ring, such as a halogen atom, e.g. fluorine, chlorine and bromine; an alkyl group e.g. methyl, ethyl, propyl, isopropyl, butyl, isobutyl, s-butyl, t-butyl and cyclohexyl; a fluoroalkyl group, e.g. difluoromethyl, trifluoromethyl, 1,1-difluoroethyl, 2,2-difluoroethyl and 1-fluoropropyl; an alkoxy group, e.g. methoxy, ethoxy, propoxy, isopropoxy, butoxy, isobutoxy, s-butoxy and t-butoxy; an acyl group, e.g. acetyl, propionyl, butyryl and isobutyryl; an acyloxy group, e.g. acetyloxy, propionyloxy, butyryloxy and isobutyryloxy; an alkoxycarbonyl group, e.g. methoxycarbonyl, ethoxycarbonyl, propoxycarbonyl, isopropoxycarbonyl, butoxycarbonyl, isobutoxycarbonyl, s-butoxycarbonyl and t-butoxycarbonyl; or a carboxylic acid group; Hal represents chlorine atom or bromine atom; and Tos-Cl represents p-tolylsulfonyl chloride.

(Description of Reaction II-a-1)

A hydroxyarene potassium salt (IV) is reacted with at least 1 molar equivalent of an arene halide (V) in the presence of activated copper powder, to yield the corresponding diarene ether (VI). The reaction is desirably carried out at the reflux temperature of the arene halide (V). After completion of the reaction, an organic solvent such as ether and water are added to the reaction mixture and extraction is effected. The diarene ether (VI) is isolated from the organic layer and purified, by vacuum distillation or like processes. [See Organic Syntheses, 2, 446(1943).]

(Description of Reaction II-a-2)

The diarene ether (VI) is reacted with 2 molar equivalents of a lithiaging agent in the presence of a solvent to yield the corresponding dilithiodiarene ether (VII). Examples of the lithiating agent are methyl lithium, butyl lithium and phenyl lithium. Examples of the solvent are diethyl ether and tetrahydrofuran. The reaction temperature is selected from a range below room temperature. [See The Journal of Organic Chemistry, 23, 10, 1476–1479(1958).]

(Description of Reaction II-a-3)

The reaction mixture prepared in Reaction II-a-2 and containing dilithiodiarene ether (VII) is reacted with at least 2 molar equivalent per mole of the dilithiodiarene ether (VII) of carbon dioxide, to yield the corresponding dicarboxydiarene ether (VIII). The reaction temperature is selected from a range below room temperature. After completion of the reaction, the reaction mixture is condensed. To the condensate an organic solvent such as ethyl acetate and water are added and extraction is effected. The dicarboxydiarene ether (VIII) is isolated from the organic layer and purified, by recrystallization or like processes. [See The Journal of Organic Chemistry, 55, 2, 438–441 (1990).]

(Description of Reaction II-a-4)

The dicarboxydiarene ether (VIII) in solid form is placed in a Soxlhet's extractor. While solvent extraction is performed intermittently, the dicarboxydiarene ether (VIII) is reacted with at least 1 molar equivalent of lithium aluminumhydride, to yield the corresponding dihydroxyalkyldiarene ether (IX). An example of the solvent used is diethyl ether. The reaction is desirably carried out at the reflux temperature of the solvent used. After completion of the reaction, the reaction mixture is condensed. Water is added to the condensate and extraction is effected. The dihydroxyalkyldiarene ether (IX) is isolated from the organic layer and purified, by recrystallization or like processes. [See The Journal of Organic Chemistry, 34, 4, 1165–1168(1969).]

(Description of Reaction II-a-5)

The dihydroxyalkyldiarene ether (IX) is reacted with 2 molar equivalents of p-toluenesulfonyl chloride in the pres ence of an amine in an amount of at least 2 molar equivalents per mole of the former, to yield the corresponding sulfonic acid ester (II-a'). An example of the amine is pyridine. The reaction temperature is selected from a range below room temperature. After completion of the reaction, the reaction mixture is condensed. The sulfonic acid ester (II-a') is isolated from the condensate and purified, by recrystallization or like processes. [See The Journal of the American Chemical Society, 74, 2, 425–428(1952).]

The halides (II-b) can be produced by any known process. For example, 2,2'-bis(bromomethyl)-di-(substituted)phenyl ether (hereinafter referred to as "halide (II-b')") and 2,2'-bis(fluoromethyl)-di(substituted)phenyl ether (hereinafter referred to as "halide (II-b")"), which belong to the category of halides (II-b), can be produced as follows.

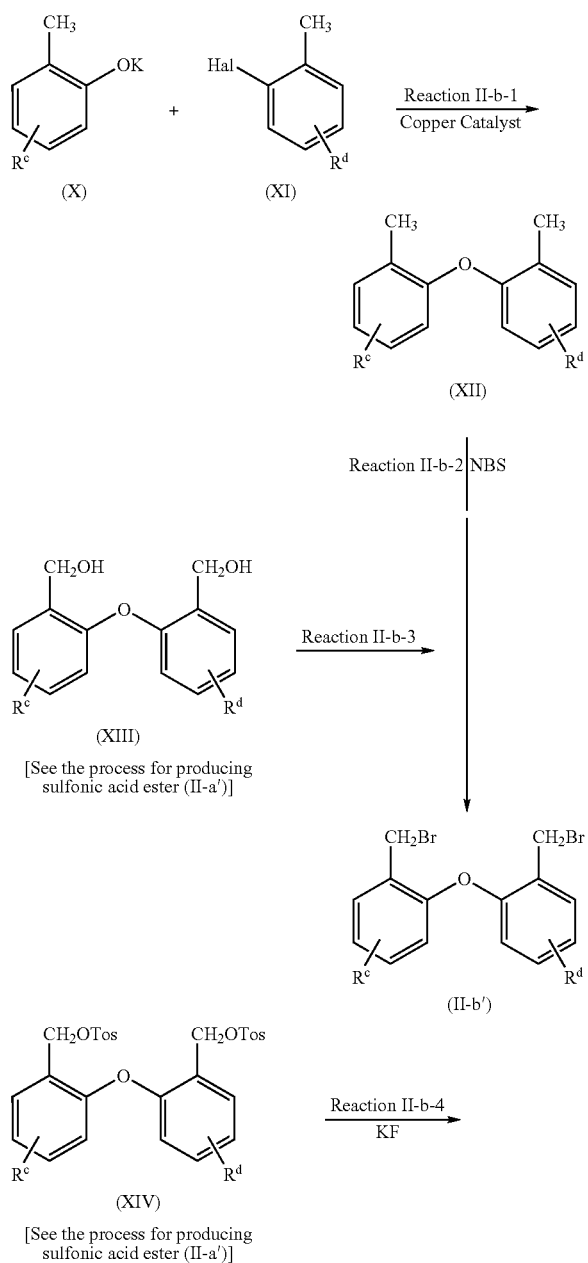

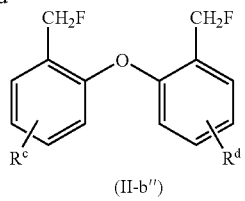

In the above formulas, $R^c$ and $R^d$ each represents a substituent on the benzene ring, such as a halogen atom, e.g. fluorine, chlorine and bromine; an alkyl group e.g. methyl, ethyl, propyl, isopropyl, butyl, isobutyl, s-butyl, t-butyl and cyclohexyl; a fluoroalkyl group, e.g. difluoromethyl, trifluoromethyl, 1,1-difluoroethyl, 2,2-difluoroethyl and 1-fluoropropyl; an alkoxy group, e.g. methoxy, ethoxy, propoxy, isopropoxy, butoxy, isobutoxy, s-butoxy and t-butoxy; an acyl group, e.g. acetyl, propionyl, butyryl and isobutyryl; an acyloxy group, e.g. acetyloxy, propionyloxy, butyryloxy and isobutyryloxy; an alkoxycarbonyl group, e.g. methoxycarbonyl, ethoxycarbonyl, propoxycarbonyl, isopropoxycarbonyl, butoxycarbonyl, isobutoxycarbonyl, s-butoxycarbonyl and t-butoxycarbonyl; or a carboxylic acid group; NBS represents N-bromosuccinimide, Hal represents chlorine or bromine atom; and Tos-Cl represents p-tolylsulfonyl chloride.

(Description of Reaction II-b-1)

A hydroxyarene potassium salt (X) is reacted with at least 1 molar equivalent of an arene halide (XI), to yield the corresponding diarene ether (XII). The reaction is desirably carried out at the reflux temperature of the arene halide (XI). After completion of the reaction, the reaction mixture is condensed. An organic solvent such as hexane and water are added to the reaction mixture and extraction is effected. The diarene ether (XII) is isolated from the organic layer and purified, by vacuum distillation or like means. [See The Journal of Organic Chemistry, 34, 4, 1165–1168(1969).]

(Description of Reaction II-b-2)

The diarene ether (XII) is reacted with at least 2 molar equivalents of N-bromosuccinimide in the presence of a solvent to yield the corresponding halide (II-b'). As the radical reaction initiator, for example benzoyl peroxide is used. An example of the solvent is carbon tetrachloride. The reaction is desirably carried out at the reflux temperature of the solvent. After completion of the reaction, the reaction mixture is filtered and the filtrate is condensed. The halide (II-b') is isolated from the condensate and purified, by recrystallization or like processes. [See The Journal of Organic Chemistry, 34, 4, 1165–1168 (1969).]

(Description of Reaction II-b-3)

The dihydroxyalkyldiarene ether (XIII) is reacted with at least 2 molar equivalent of hydrogen bromide in the presence of a solvent, to yield the corresponding halide (II-b'). An example of the solvent is benzene. The reaction temperature is selected from a range below room temperature. After completion of the reaction, the reaction mixture is condensed. The halide (II-b') is isolated from the condensate and purified, by recrystallization or like processes. [See The Journal of Organic Chemistry, 34, 4, 1165–1168(1969).]

(Description of Reaction II-b-4)

The sulfonic acid ester (XIV) is reacted with at least 2 molar equivalents of potassium fluoride in the presence of a solvent, to yield the corresponding halide (II-b"). An example of the solvent used is diethylene glycol. The reaction temperature is selected from a range below 130° C. After completion of the reaction, the halide (II-b") is isolated from the reaction mixture and purified, by vacuum distillation or like processes. [See Chemistry Letters, 3, 265–268 (1982).]

The alkali metal phosphides (III) can be produced by any known method. For example, alkali metal phosphides with M in the general formula (III) being lithium atom can be obtained by reacting the corresponding phosphines with a lithiaging agent. Alkali metal phosphide with M in the general formula (III) being sodium or potassium atom can be obtained by reacting the corresponding phosphine halides with metallic sodium or metallic potassium [See Chemische Berichte, 92, 1118–1126(1959)].

The Group VIII metal complexes (A) comprising a bisphosphine (I) and a Group VIII metal compound are novel compounds that have not been described in the literature. These complexes can act as catalysts for hydroformylation and exert high catalytic activity. These complexes can, when used for hydroformylation of ethylenically unsaturated compounds, produce n-aldehydes with high selectivity and suppress side reactions such as hydrogenation and isomerization.

The group VIII metal compound used for this purpose should either originally have the catalytic activity to accelerate hydroformylation of ethylenically unsaturated compounds or acquire such catalytic activity under reaction conditions for the hydroformylation. Examples of such metal compound are those rhodium compounds, cobalt compounds, ruthenium compounds and iron compounds that have been used as catalysts for hydroformylation. Examples of the rhodium compounds are rhodium oxides, e.g. RhO, $RhO_2$, $Rh_2O$ and $Rh_2O_3$; rhodium salts, e.g. rhodium nitrate, rhodium sulfate, rhodium chloride, rhodium iodide and rhodium acetate; and rhodium complexes, e.g. $Rh(acac)(CO)_2$, $RhCl(CO)(PPh_3)_2$, $RhCl(CO)(AsPh_3)_2$, $RhCl(PPh_3)_3$, $RhBr(CO)(PPh_3)_2$, $Rh_4(CO)_{12}$, and $Rh_6(CO)_{16}$. Examples of the cobalt compounds are cobalt complexes, e.g. $HCo(CO)_3$, $HCo(CO)_4$, $Co_2(CO)_8$ and $HCo_3(CO)_9$. Examples of the ruthenium compounds are ruthenium complexes, e.g., $Ru(CO)_3(PPh_3)_2$, $RuCl_2(PPh_3)_3$, $RhCl_3(PPh_3)_3$ and $Ru_3(CO)_{12}$. Examples of the iron compounds are iron complexes, e.g. $Fe(CO)_5$, $Fe(CO)_4PPh_3$ and $Fe(CO)_4(PPh_3)_2$. Among these compounds, it is preferable to use rhodium compounds, for which mild conditions can be selected for hydroformylation, in particular $Rh(acac)(CO)_2$.

The bisphophines (I) may be used singly or in combination of 2 or more, or further in combination with another phosphorous compound. Examples of such other phosphorous compounds are phosphine, e.g. triethylphosphine, triisopropylphosphine, tributylphosphine, tricyclohexylphosphine, tribenzylphosphine, dimethylphenylphosphine, diethylphenylphosphine, methyldiphenylphosphine, ethyldiphenylphosphine, butyldiphenylphosphine, cyclohexyldiphenylphosphine, 2-furyldiphenylphosphine, 2-pyridyldiphenylphosphine, 4-pyridyldiphenylphosphine, triphenylphosphine, o-tolyldiphenylphosphine, diphenyl(pentafluorophenyl)phosphine, m-diphenylphosphinobenzenesulfonic acid and metal salts thereof, p-diphenylphosphinobenzoic acid and metal salts thereof, p-diphenylphosphinophosphonic acid and metal salts thereof, p-diphenylphosphinobenzenesulphonic acid and metal salts thereof, bis(pentafluorophenyl)phenylphosphine, tris(p-fluorophenyl)phosphine, tris(pentafluorophenyl)phosphine, tris(p-chlorophenyl)phosphine, tri-o-tolylphosphine, tri-m-tolylphosphine, tri-p-tolylphosphine, tris(p-methoxyphenyl)phosphine and tris(p-N,N-dimethylaminophenyl)phosphine; and phosphites, e.g. triethyl phosphite, triphenyl phosphite, tris(p-methylphenyl)phosphite, tris(p-trifluoromethylphenyl)phosphite, tris(p-methoxyphenyl)phosphite, tris(2,4-dimethylphenyl)phosphite and tris(2,4-di-t-butylphenyl)phosphite.

The bisphosphine (I) is used desirably in an amount of 2 to 10000 moles in terms of phosphorus atom per mole of the group VIII metal compound used in terms of said group VIII metal atom, more preferably 2 to 1000 moles in the same terms. If the amount of the bisphosphine (I) is less than this range, the catalyst will become unstable. Amounts exceeding this range increase catalyst cost.

There are no specific restrictions with respect to the preparation process for the Group VIII metal complex (A). For example, the complex can be prepared by a process which comprises separately preparing a solution of a Group VIII metal compound in a solvent that does not influence the hydroformylation and a solution of a bisphosphine (I) prepared in the same manner, introducing the two solutions separately into a hydroformylation reactor and effecting reaction therein to produce a complex. The complex can also be prepared by introducing a bisphosphine (I) into the above Group VIII metal compound solution and then adding a solvent that does not affect the hydroformylation, to obtain a homogeneous solution.

The process for hydroformylation of ethlenically unsaturated compounds with carbon monoxide and hydrogen in the presence of a Group VIII metal complex (A), to produce the corresponding aldehydes is now described.

Ethylenically unsaturated compounds usable for this process can be any of linear, branched and cyclic olefins, which have carbon-carbon double bond in terminal or internal. Examples of such ethylenically unsaturated compounds are unsaturated aliphatic hydrocarbons, e.g. ethylene, propylene, 1-butene, 1-pentene, 1-hexene, 1-heptene, 1-octene, 1-nonene, 2-butene, isobutene, 2-octene, 1,7-octadiene, vinylcyclohexene, cyclooctadiene, dicyclopentadiene, butadiene polymers and isoprene polymers; styrenes, e.g. styrene, α-methylstyrene, β-methylstyrene, alkyl group-ring substituted styrenes and divinylbenzene; alicyclic olefin hydrocarbons, e.g. cyclopentene, cyclohexene, 1-methylcyclohexene, cyclooctene and limonene; and functional group-containing olefins, e.g. allyl alcohol, crotyl alcohol, 3-methyl-3-buten-1-ol, 7-octen-1-ol, 2,7-octadienol, vinyl acetate, allyl acetate, methyl acrylate, ethyl acrylate, methyl methacrylate, allyl acrylate, vinyl methyl ether, allyl ethyl ether, 5-hexenamide, acrylonitrile and 7-octen-1-al.

The Group VIII metal complex (A) is used desirably in an amount of 0.0001 to 1000 milligram-atom in terms of group VIII metal atom per liter of the reaction liquid, more preferably in an amount of 0.005 to 10 milligram-atom in the same terms. Too small an amount of the Group VIII metal complex (A) results in too low a reaction rate, while amounts exceeding this range increase the catalyst cost.

The hydroformylation is carried out either in the presence or absence of a solvent. Examples of solvents usable for this purpose are aromatic hydrocarbons, e.g. benzene, toluene, ethylbenzene, propylbenzene, butylbenzene, isobutylbenzene, s-butylbenzene, t-butylbenzene, o-xylene, m-xylene, p-xylene, o-ethyltoluene, m-ethyltoluene and p-ethyltoluene; saturated aliphatic hydrocarbons, pentane, hexane, heptane, octane, nonane, decane and cyclohexane; alcohols, e.g. methyl alcohol, ethyl alcohol, propyl alcohol, isopropyl alcohol, butyl alcohol, isobutyl alcohol, s-butyl alcohol, t-butyl alcohol, pentyl alcohol, isopentyl alcohol, neopentyl alcohol, t-pentyl alcohol, 2-phenylethanol and 2-phenoxyethanol; ethers, e.g. dimethyl ether, ethylmethyl ether, diethylether, dipropyl ether, butyl methyl ether, t-butyl methyl ether, dibutyl ether, ethyl phenyl ether, diphenyl ether, tetrahydrofuran, 1,4-dioxane, ethylene glycol, propylene glycol, diethylene glycol, ethylene glycol monomethyl ether, ethylene glycol dimethyl ether, diethylene glycol diethyl ether, triethylene glycol, triethylene glycol dimethyl ether, tetraethylene glycol, tetraethylene glycol dimethyl ether, polyethylene glycol, polypropylene glycol, polyethylene glycol monomethyl ether, polyethylene glycol dimethyl ether and polyethylene glycol diethyl ether; esters, e.g. methyl acetate, ethyl acetate, propyl acetate, butyl acetate, isopentyl acetate, phenyl acetate, methyl propionate, ethyl propionate, methyl benzoate and ethyl benzoate; ketones, e.g. acetone, ethyl methyl ketone, methyl propyl ketone, ethyl ketone, ethyl propyl ketone, dipropyl ketone, acetophenone, ethyl phenyl ketone, 1-phenyl-1-propanone, 1-phenyl-1-butanone and 1-phenyl-2-propaneone; halohydrocarbons, e.g. chloromethane, dichloromethane, trichloromethane, tetrachloromethane, chloroethane, 1,1-dichloroethane, 1,2-dichloroethane, 1,1,1-trichloroethane, 1,1,2-trichloroethane, 1,1,2,2-tetrachloroethane, 1,2-dichlorohexane, chlorobenzene, o-dichlorobenzene, m-dichlrobenzene, p-dichlrobenzene, 1,2,3-trichlrobenzene, 1,2,4-trichlorobenzene, 1,3,5-trichlorobenzene, fluoroethane, difluoromethane, 1,1-difluoroethane, fluorobenzene, o-fluorotoluene, m-fluorotoluene, p-fluorotoluene and α,α,α-trifluorotoluene; cyanohydrocarbons, e.g. acetonitrile, propionitrile, 1-cyanopropane, cyanobenzene, o-cyanotoluene, m-cyanotoluene and p-cyanotoluene; aprotic polar solvents, e.g N,N-dimethylformamide, hexamethylphosphoramide, 1,3-dimethyl-2-imidazolidinone and 1-methyl-2-pyrrolidinone; and water. These solvents may be used singly or in combination of 2 or more. There is no particular limitation to the amount of the solvent used.

It is desirable that the mixed gas of hydrogen and carbon monoxide used for the hydroformylation have a $H_2/CO$ molar ratio ranging from 0.1 to 10, more preferably from 0.5 to 2, which ensures easy maintenance of the mixed gas composition. The reaction pressure is desirably set to 0.1 to 10 Mpa, more preferably 0.2 to 5 Mpa, in view of reaction rate. The reaction temperature is desirably in a range of 40 to 150° C., more preferably in a range of 60 to 130° C., which can suppress deactivation of the catalyst used. The reaction can be carried out in any of stirred-type, liquid circulation-type, gas circulation-type, bubbled column-type and like reactors. The reaction can be carried out either continuously or batchwise.

Although there are no specific restrictions with respect to the method of feeding starting materials, it is desirable to feed an ethylenically unsaturated compound, a Group VIII metal complex (A) solution prepared separately and, as necessary, a solvent and then introduce a mixed gas of hydrogen and carbon monoxide under a prescribed pressure. Then the reaction is desirably effected with stirring at a prescribed temperature.

The aldehydes obtained by the above process can be isolated and purified by any one of known processes. For example, the reaction mixture is distilled to remove the solvent and unreacted ethylenically unsaturated compound, and the distillation residue is distilled to isolate and yield the product aldehyde with high purity. Or, prior to the distillation the catalyst component may be separated by evaporation, extraction, adsorption or like known processes.

EXAMPLES

Hereinbelow, the present invention is described more concretely by reference to specific examples which are by no means limitative of the invention. In the Examples that follow, unless otherwise specified, synthesis of phosphorus compounds was carried out under an atmosphere of nitrogen or argon, and hydroformylations were all carried out under an atmosphere of a mixed gas having a $H_2/CO$ ratio of 1.

Bisphosphines (I) and their precursors were identified with $^1$H-NMR spectrograph (GSX-270, made by JEOL, LTd.) and/or $^{31}$P-NMR spectrograph (Lambda-500, made by JEOL, Ltd.). The values of chemical shifts of $^{31}$P-NMR were based on the chemical shift of phosphoric acid set to 0 ppm, where the latter had been previously determined on 20% by weight phosphoric acid in deuterated water.

Reference Example 1

Synthesis of 2,2'-dimethyldiphenyl ether

A 1-liter three-necked flask equipped with a reflux condenser, a Dean-Stark apparatus, a dropping funnel, a thermometer and a mechanical stirrer was charged with 40 g (0.71 mole) of potassium hydroxide, 77 g (0.71 mole) of o-cresol, 100 g (0.79 mole) of 2-chlorotoluene and 400 g (2.34 moles) of 2-bromotoluene. The three-necked flask was heated at 150° C., while the water that generated was continuously removed from the flask using the Dean-Stark apparatus. Then 3 g of activated copper powder was added and, while the water contained in the activated copper and 2-chlorotoluene were continuously removed from the reaction liquid, the flask was heated up to a liquid temperature of 190° C. Stirring was continued for 10 hours at the same temperature. After completion of the reaction, the reaction mixture was allowed to cool to room temperature. To the mixture 400 ml of diethyl ether was added, and the obtained solution was filtered through Celite. The filtrate was washed 5 times each with 200 ml of 5% by weight aqueous potassium hydroxide solution. The organic layer thus obtained was distilled in vacuo at 0.3 mmHg, to give 84 g of a distillate at 93° C. This distillate was colorless oily matter and found to be 2,2'-dimethyldiphenyl ether having the following properties. The yield was 60% based on the o-cresol.

$^1$H-NMR (270 MHz, deuterated benzene, TMS, ppm) δ: 2.18 (s, 6H, Ar—C$\underline{H}_3$), 6.67 (d, 2H), 6.80–7.00 (m, 4H), 7.05 (d, 2H).

Reference Example 2

Synthesis of 2,2'-bis(bromomethyl)diphenyl ether

A 500-ml three-necked flask equipped with a reflux condenser, a thermometer and a mechanical stirrer was charged with 250 ml of carbon tetrachloride, 58 g (0.33 mole) of N-bromosuccinimide and 32 g (0.16 mole) of the 2,2'-dimethyldiphenyl ether synthesized in Reference Example 1. The contents were refluxed at a liquid temperature of 70° C. Then 1 g of benzoyl peroxide was added in 3 portions over 30 minutes and the contents were further stirred for 30 minutes. The reaction mixture thus obtained was filtered and the filtrate was condensed and dried. The dried matter was recrystallized from a solvent of hexane, to yield 20 g of a colorless crystal 2,2'-bis(bromomethyl) diphenyl ether having the following properties. The yield was 35% based on the 2,2'-dimethyldiphenyl ether.

¹H-NMR (270 MHz, deuterated benzene, TMS, ppm) δ: 4.30 (s, 4H, Ar—C$\underline{H}_2$—Br), 6.58 (d, 2H), 6.73 (t, 2H), 6.83 (t, 2H), 7.04 (d, 2H).

Reference Example 3

Synthesis of 2-hydroxy-3-methoxytoluene

A 3-liter three-necked flask equipped with a thermometer and a mechanical stirrer was charged with 300 g (1.97 moles) of o-vanillin, 100 g of palladium-carbon supporting 5% by weight of palladium, 2 liters of ethyl acetate and 500 ml of acetic acid. The contents were stirred under a hydrogen atmosphere and at room temperature, for 84 hours. The reaction mixture thus obtained was filtered and the filtrate was condensed. To the condensate, 2 liters of ethyl acetate was added again, and the mixture was washed with 1 liter of water three times. The obtained organic layer was condensed and cooled, to yield 259 g of colorless crystal of 2-hydroxy-3-methoxytoluene having the following properties. The yield was 95% based on the o-vanillin.

¹H-NMR (270 MHz, deuterated benzene, TMS, ppm) δ: 2.28 ( s, 3H, Ar—C$\underline{H}_3$), 3.19 (s, 3H, Ar—O—C$\underline{H}_3$), 5.78 (s, 1H, Ar—O$\underline{H}$), 6.38 (d, 1H), 6.63–6.80 (m, 2H).

Reference Example 4

Synthesis of 2,2'-dimethyl-6-methoxy-diphenyl ether

A 1-liter three-necked flask equipped with a reflux condenser, a Dean-Stark apparatus, a dropping funnel, a thermometer and a mechanical stirrer was charged with 500 ml of toluene, 36.5 g (0.65 mole) of potassium hydroxide and 90 g (0.65 mole) of the 2-hydroxy-3-methoxytoluene synthesized in Reference Example 3. The three-necked flask was heated at 120° C., while the water that generated was continuously removed from the flask using the Dean-Stark apparatus. After the water removal, the solvent was removed mostly under reduced pressure. To the mixture, 10 g of activated copper powder and 700 g (4.1 moles) of 2-bromotoluene were added and, while the water that generated was continuously removed from the reaction liquid using the Dean-Stark apparatus, the flask was heated up to a liquid temperature of 190° C. Stirring was continued for 10 hours at the same temperature. After completion of the reaction, the reaction mixture was allowed to cool to room temperature. To the mixture 400 mL of diethyl ether was added, and the obtained solution was filtered through Celite. The filtrate was distilled under a reduced pressure of 0.5 mmHg, to give a distillate at 120° C. This distillate was recrystallized from a solvent of hexane, to yield 90 g of a colorless crystal of 2,2'-dimethyl-6-methoxy-diphenyl ether having the following properties. The yield was 61% based on the 2-hydroxy-3-methoxytoluene.

¹H-NMR (270 MHz, deuterated benzene, TMS, ppm) δ:2.09 (s, 3H, Ar—C$\underline{H}_3$), 2.49 (s, 3H, Ar—C$\underline{H}_3$), 3.18 (s, 3H, Ar—O—C$\underline{H}_3$), 6.50 (dd, 2H), 6.68–6.99 (m, 4H), 7.09 (d, 1H).

Reference Example 5

Synthesis of 2,2'-bis(bromomethyl)-6-methoxy-diphenyl ether

A 1-liter three-necked flask equipped with a reflux condenser, a thermometer and a mechanical stirrer was charged with 450 ml of carbon tetrachloride, 81 g (0.46 mole) of N-bromosuccinimide and 52 g (0.23 mole) of the 2,2'-dimethyl-6-methoxy-diphenyl ether synthesized in Reference Example 4. The contents were refluxed at a liquid temperature of 70° C. Then 1 g of benzoyl peroxide was added in 3 portions over 30 minutes and the contents were further stirred for 30 minutes. The reaction mixture thus obtained was filtered and the filtrate was condensed and dried. The dried matter was recrystallized from a solvent of hexane, to yield 40 g of a colorless crystal of 2,2'-bis (bromomethyl)-6-methoxy-diphenyl ether having the following properties. The yield was 45% based on the 2,2'-dimethyl-6-methoxy-diphenyl ether.

¹H-NMR (270 MHz, deuterated benzene, TMS, ppm) δ: 3.04 (s, 3H, Ar—O—C$\underline{H}_3$), 4.29 (s, 2H, Ar—C$\underline{H}_2$—Br), 4.57 (s, 2H, Ar—C$\underline{H}_2$—Br), 6.34–6.45 (m, 2H), 6.67 (t, 1H), 6.76–6.88 (m, 3H), 7.06 (d, 1H).

Example 1

Synthesis of 2,2'-bis(diphenylphosphinomethyl)-diphenyl ether

A 500-ml three-necked flask equipped with a reflux condenser, a dropping funnel, a thermometer and a magnetic rotor was charged with 250 ml of tetrahydrofuran, and then 20 g (0.11 mole) of diphenylphosphine. The contents were cooled down to a liquid temperature of −75° C. Thereafter, 69 ml (0.11 mole) of a 1.56 mole/l solution of butyl lithium in hexane was added dropwise over 2 hours at such a rate as to maintain the liquid temperature at −75 to −65° C. The contents were stirred for 1 hour at the same temperature, to yield lithium diphenylphosphide. To the solution, a solution of 19 g (0.054 mole) of the 2,2'-bis(bromomethyl)diphenyl ether synthesized in Reference Example 2 in 100 ml of tetrahydrofuran was added dropwise over 2 hours at such a rate as to maintain the liquid temperature at −75 to −65° C. The mixture was allowed to warm up to room temperature and stirred for 1 hour. After completion of the reaction, 250 ml of tetrahydrofuran was distilled off from the reaction mixture. To the residue, 200 ml of diethyl ether was added. The solution thus obtained was washed 3 times with 150 ml of saturated aqueous ammonium chloride solution and 3 times with 150 ml of water, to be subjected to extraction. The organic layer obtained was dried over anhydrous magnesium sulfate and then filtered. The obtained filtrate was condensed to give an oily residue. To the condensate 200 ml of methanol was added and the mixture was boiled at the reflux temperature of the solvent for 10 minutes, to yield 26 g of white powder of 2,2'-bis(diphenylphosphinomethyl) diphenyl ether having the following properties. The yield was 85% based on the 2,2'-bis(bromomethyl)diphenyl ether.

¹H-NMR (270 MHz, deuterated benzene, TMS, ppm) δ: 3.60 (s, 4H, Ar—C$\underline{H}_2$—P), 6.67–6.78 (m, 4H), 6.85 (t, 2H), 6.95–7.10 (m, 14H, of which 12H are P(C$_6\underline{H}_5$)$_2$), 7.36–7.50 (m, 8H, P(C$_6\underline{H}_5$)$_2$).

³¹P-NMR (500 MHz, deuterated benzene, phosphoric acid solution in deuterated water, ppm) δ: −11.2 (s).

Example 2

A 1-liter three-necked flask equipped with a reflux condenser, a dropping funnel, a thermometer and a magnetic rotor was charged with 200 ml of dibutyl ether, and then 10 g (0.44 mole) of metallic sodium. The contents were stirred at 100° C. for 0.5 hour, to give a dispersion of metallic sodium. To the dispersion, 48 g (0.22 mole) of chlorodiphenylphosphine was added dropwise over 2 hours at such a rate as to maintain the liquid temperature at 100 to 110° C. After the addition the mixture was stirred for 1 hour at the same temperature, to give sodium diphenylphosphide. The solution was then cooled to a temperature of 35° C., and 500 ml of tetrahydrofuran was added. To the mixture, a solution of 39 g (0.11 mole) of the 2,2'-bis(bromomethyl)diphenyl ether synthesized in Reference Example 2 in 200 ml of tetrahydrofuran was added dropwise over 2 hours at such a rate as to maintain the liquid temperature at −75 to −65° C. The mixture was allowed to warm up to room temperature and stirred for 1 hour. After completion of the reaction, the solvent was mostly distilled off from the reaction mixture. To the residue, 400 ml of diethyl ether was added. The solution thus obtained was washed by extracting 3 times with 300 ml of saturated aqueous ammonium chloride solution and 3 times with 300 ml of water. The organic layer obtained was dried over anhydrous magnesium sulfate and then filtered. The obtained filtrate was condensed to give an oily residue. To the condensate 400 ml of methanol was added and the mixture was boiled at the reflux temperature of the solvent for 10 minutes, to yield 42 g of white powder of 2,2'-bis(diphenylphosphinomethyl)diphenyl ether having the above-described properties. The yield was 68% based on the 2,2'-bis(bromomethyl)diphenyl ether.

Example 3

Synthesis of 2,2'-bis(diphenylphosphinomethyl)-6-methoxy-diphenyl ether

A 500-ml three-necked flask equipped with a reflux condenser, a dropping funnel, a thermometer and a magnetic rotor was charged with 200 ml of tetrahydrofuran, and then 9 g (0.049 mole) of diphenylphosphine. The contents were cooled to a liquid temperature of −75° C. To the mixture, 31.5 ml (0.049 mole) of a 1.56 mole/l butyl lithium solution in hexane was added dropwise over 2 hours at such a rate as to maintain the liquid temperature at −75 to −65° C. After the addition the mixture was stirred for 1 hour at the same temperature. To the mixture, a solution of 9.5 g (0.024 mole) of the 2,2'-bis(bromomethyl)-6-methoxy-diphenyl ether synthesized in Reference Example 5 in 100 ml of tetrahydrofuran was added dropwise over 2 hours at such a rate as to maintain the liquid temperature at −75 to −65° C. The mixture was allowed to warm up to room temperature and stirred for 1 hour. Then the mixture was allowed to warm up to room temperature and stirred for 1 hour. After completion of the reaction, 250 ml of the tetrahydrofuran was distilled off from the reaction mixture. To the residue, 200 ml of diethyl ether was added. The solution thus obtained was washed by extracting 3 times with 150 ml of saturated aqueous ammonium chloride solution and 3 times with 150 ml of water. The organic layer obtained was dried over anhydrous magnesium sulfate and then filtered. The obtained filtrate was condensed to give an oily residue. To the condensate 20 ml of methanol was added and the mixture was cooled to −50° C., to yield white solid, and this procedure was repeated 3 times. The white powder thus obtained was dried under reduced pressure, to give 10 g of white powder of 2,2'-bis(diphenylphosphinomethyl)-6-methoxy-diphenyl ether having the following properties. The yield was 70% based on the 2,2'-bis(bromomethyl)-6-methoxy-diphenyl ether.

$^1$H-NMR (270 MHz, deuterated benzene, TMS, ppm) δ: 3.13 s, 3H, Ar—O—C$\underline{H}_3$), 3.71 (s, 4H, Ar—C$\underline{H}_2$—P), 6.42 (d, 1H), 6.53–6.66 (m, 2H), 6.77–6.92 (m, 4H), 6.92–7.10 (m, 12H, P(C$_6$$\underline{H}_5$)$_2$), 7.32–7.58 (m, 8H, P(C$_6$$\underline{H}_5$)$_2$). $^{31}$P-NMR (500 MHz, deuterated benzene, phosphoric acid solution in deuterated water, ppm) δ: −14.0 (s, 1P, MeO—Ar—CH$_2$—$\underline{P}$), −11.4 ppm (s, 1P, Ar—CH$_2$—$\underline{P}$).

Example 4

Hydroformylation of 7-octen-1-al using a catalyst of 2,2'-bis(diphenylphosphinomethyl)diphenyl ether-Rhodium complex A 100-ml three-necked flask equipped with a Teflon magnetic rotor was charged with 3.9 mg (0.015 mmole) of Rh(acac)(CO)$_2$ and 84.9 mg (0.15 mmole) of the 2,2'-bis(diphenylphosphinomethyl)diphenyl ether synthesized in Example 1, and further with 6 ml of toluene. The mixture was stirred at 50° C. for 30 minutes to become a homogeneous catalyst solution. A 50-ml three-necked flask equipped with a Teflon magnetic rotor was charged with 3 ml of this catalyst solution and 27 ml (0.167 mole; purity: 93%) of 7-octen-1-al. The mixture was then fed to a 100-ml autoclave equipped with a gas inlet and a sampling port. The inside pressure was raised with the mixed gas to 3.0 Mpa. With stirring the inside temperature was raised to 85° C. and reaction was effected for 6 hours, to obtain 20.6 g (0.132 mole; yield: 79%) of 1,9-nonanedial and 4.2 g (0.027 mole; yield: 16%) of 2-methyl-1,8-octanedial. The conversion of 7-octen-1-al was 95% and the selectivities to n-aldehyde and iso-aldehyde were 83% and 18%, respectively. The n/iso ratio was 4.88. No side reactions such as hydrogenation and isomerization were observed.

Example 5

Example 4 was repeated except that the inside pressure was changed from 3.0 Mpa to 0.5 Mpa and that the reaction time was changed from 6 hours to 4 hours, to obtain 22.2 g (0.142 mole; yield: 85%) of 1,9-nonanedial and 1.3 g (0.008 mole; yield: 5%) of 2-methyl-1,8-octanedial. The conversion of 7-octen-1-al was 97% and the selectivities to n-aldehyde and iso-aldehyde were 88% and 5%, respectively. The n/iso ratio was 17.6. The ratio of side reactions such as hydrogenation and isomerization was 7%.

Example 6

Example 4 was repeated except that 42.5 mg (0.075 mmole) of 2,2'-bis(diphenylphosphinomethyl)diphenyl ether was used, that the inside pressure was changed from 3.0 Mpa to 0.5 Mpa and that the reaction time was changed from 6 hours to 4 hours, to obtain 21.8 g (0.139 mole; yield: 84%) of 1,9-nonanedial and 1.5 g (0.010 mole; yield: 6%) of 2-methyl-1,8-octanedial. The conversion of 7-octen-1-al was 96% and the selectivities to n-aldehyde and iso-aldehyde were 87% and 6%, respectively. The n/iso ratio was 14.5. The ratio of side reactions such as hydrogenation and isomerization was 7%.

Example 7

Hydroformylation of 7-octen-1-al using a catalyst of 2,2'-bis(diphenylphosphinomethyl)-6-methoxy-diphenyl ether-Rhodium complex Example 4 was repeated except that 89.5 mg of the 2,2'-bis(diphenylphosphinomethyl)-6-methoxy-diphenyl ether synthesized in Example 3 was used instead of 84.9 mg (0.15 mmole) of 2,2'-bis(diphenylphosphinomethyl)diphenyl ether was used, and that the reaction time was changed from 6 hours to 8 hours, to obtain 21.1 g (0.135 mole; yield: 81%) of 1,9-nonanedial and 4.0 g (0.026 mole; yield: 15%) of 2-methyl-1,8-octanedial. The conversion of 7-octen-1-al was 96% and the selectivities to n-aldehyde and iso-aldehyde were 84% and 16%, respectively. The n/iso ratio was 5.25. No side reactions such as hydrogenation and isomerization were observed.

Example 8

Hydroformylation of 1-octene using a catalyst of 2,2'-bis(diphenylphosphinomethyl)diphenyl ether-Rhodium complex A 100-ml three-necked flask equipped with a Teflon magnetic rotor was charged with 3.9 mg (0.015 mmole) of Rh(acac)(CO)$_2$ and 42.5 mg (0.075 mmole) of the 2,2'-bis(diphenylphosphinomethyl)diphenyl ether synthesized in Example 1, and further with 6 ml of toluene. The mixture was stirred at 50° C. for 30 minutes to become a homogeneous catalyst solution. A 50-ml three-necked flask equipped with a Teflon magnetic rotor was charged with 3 ml of this catalyst solution and 27 ml (0.172 mole; purity: at least 99%) of 1-octene. The mixture was then fed to a 100-ml autoclave equipped with a gas inlet and a sampling port. The inside pressure was raised with the mixed gas to 1.0 Mpa. With stirring the inside temperature was raised to 85° C. and reaction was effected for 5 hours, to obtain 21.2 g (0.149 mole; yield: 87%) of nonanal and 1.5 g (0.011 mole; yield: 6%) of 2-methyloctanal. The conversion of 1-octene was 98% and the selectivities to n-aldehyde and iso-aldehyde were 89% and 6%, respectively. The n/iso ratio was 14.8. The ratio of side reactions such as hydrogenation and isomerization was 5%.

Example 9

Hydroformylation of 1-octene using a catalyst of 2,2'-bis(diphenylphosphinomethyl)-6-methoxy-diphenyl ether-Rhodium complex Example 8 was repeated except that 44.8 mg (0.075 mmole) of the 2,2'-bis(diphenylphosphinomethyl)-6-methoxy-diphenyl ether synthesized in Example 3 was used instead of 42.5 mg (0.075 mmole) of the 2,2'-bis(diphenylphosphinomethyl)diphenyl ether, to obtain 21.3 g (0.150 mole; yield: 87%) of nonanal and 1.5 g (0.010 mole; yield: 6%) of 2-methyloctanal. The conversion of 1-octene was 98% and the selectivities to n-aldehyde and iso-aldehyde were 89% and 6%, respectively. The n/iso ratio was 14.8%. The ratio of side reactions such as hydrogenation and isomerization was 5%.

Comparative Example 1

Hydroformylation of 7-octen-1-al using a catalyst of triphenylphosphine-Rhodium complex Example 4 was repeated except that 78.7 mg (0.3 mmole) of triphenylphosphine was used instead of 84.9 mg (0.15 mmole) of 2,2'-bis(diphenylphosphinomethyl)diphenyl ether, and that the reaction time was changed from 6 hours to 8 hours, to obtain 17.8 g (0.114 mole; yield: 68%) of 1,9-nonanedial and 7.0 g (0.045 mole; yield: 27%) of 2-methyl-1,8-octanedial. The conversion of 7-octen-1-al was 95% and the selectivities to n-aldehyde and iso-aldehyde were 72% and 28%, respectively. The n/iso ratio was 2.57. No side reactions such as hydrogenation and isomerization were observed.

Comparative Example 2

Hydroformylation of 7-octen-1-al using a catalyst of BISBI-Rhodium complex

Example 4 was repeated except that 82.6 mg (0.15 mmole) of BISBI was used instead of 84.9 mg (0.15 mmole) of 2,2'-bis(diphenylphosphinomethyl)diphenyl ether, and that the reaction time was changed from 6 hours to 10 hours, to obtain 23.1 g (0.148 mole; yield: 88%) of 1,9-nonanedial and 0.7 g (0.005 mole; yield: 3%) of 2-methyl-1,8-octanedial. The conversion of 7-octen-1-al was 95% and the selectivities to n-aldehyde and iso-aldehyde were 93% and 3%, respectively. The n/iso ratio was 31.00. The selectivity to side reactions such as hydrogenation and isomerization was 4%.

Comparative Example 3

Hydroformylation of 7-octen-1-al using a catalyst of Xantphos-Rhodium complex

Example 4 was repeated except that 86.7 mg (0.15 mmole) of Xantphos was used instead of 84.9 mg (0.15 mmole) of 2,2'-bis(diphenylphosphinomethyl)diphenyl ether, and that the reaction time was changed from 6 hours to 15 hours, to obtain 22.1 g (0.141 mole; yield: 85%) of 1,9-nonanedial and 0.9 g (0.006 mole; yield: 4%) of 2-methyl-1,8-octanedial. The conversion of 7-octen-1-al was 89% and the selectivities to n-aldehyde and iso-aldehyde were 95% and 4%, respectively. The n/iso ratio was 23.75. The selectivity to side reactions such as hydrogenation and isomerization was 1%.

Comparative Example 4

Hydroformylation of 1-octene using a catalyst of triphenylphosphine-Rhodium complex Example 8 was repeated except that 39.4 mg (0.15 mmole) of triphenylphosphine was used instead of 42.5 mg (0.075 mmole) of 2,2'-bis(diphenylphosphinomethyl)diphenyl ether and that the reaction time was changed from 5 hours to 8 hours, to obtain 16.4 g (0.115 mole; yield: 67%) of nonanal and 5.5 g (0.039 mole; yield: 22%) of 2-methyloctanal. The conversion of 1-octene was 98% and the selectivities to n-aldehyde and iso-aldehyde were 68% and 23%, respectively. The n/iso ratio was 2.96. The ratio of side reactions such as hydrogenation and isomerization was 9%.

Comparative Example 5

Hydroformylation of 1-octene using a catalyst of BISBI-Rhodium complex

Example 8 was repeated except that 41.3 mg (0.075 mmole) of BISBI was used instead of 42.5 mg (0.075 mmole) of 2,2'-bis(diphenylphosphinomethyl)diphenyl ether and that the reaction time was changed from 5 hours to 10 hours, to obtain 21.4 g (0.151 mole; yield: 88%) of nonanal and 0.29 g (0.002 mole; yield: 1%) of 2-methyloctanal. The conversion of 1-octene was 98% and the selectivities to n-aldehyde and iso-aldehyde were 89% and 1%, respectively. The n/iso ratio was 89.0. The ratio of side reactions such as hydrogenation and isomerization was 10%.

Comparative Example 6

Hydroformylation of 1-octene using a catalyst of Xantphos-Rhodium complex

Example 8 was repeated except that 43.4 mg (0.075 mmole) of Xantphos was used instead of 42.5 mg (0.075 mmole) of 2,2'-bis(diphenylphosphinomethyl)diphenyl ether and that the reaction time was changed from 5 hours to 15 hours, to obtain 19.4 g (0.136 mole; yield: 79%) of nonanal and 0.39 g (0.003 mole; yield: 2%) of 2-methyloctanal. The conversion of 1-octene was 86% and the selectivities to n-aldehyde and iso-aldehyde were 92% and 2%, respectively. The n/iso ratio was 46.0. The ratio of side reactions such as hydrogenation and isomerization was 6%.

In the hydroformylation of 7-octen-1-al, comparison of Examples 4 and 7 with Comparative Examples 2 and 3 reveals that Group VIII metal complexes (A) comprising bisphosphines can exert higher catalytic activity than Group VIII metal complexes comprising known bisphosphines and, further, cause no side reactions such as hydrogenation and isomerization. Besides, as shown in Examples 5 and 6, changing the reaction conditions employed in Example 4 can increase the n/iso ratio and catalytic activity. On the other hand, comparison of Examples 4 and 7 with Comparative Example 1 reveals that Group VIII metal complexes (A) comprising bisphosphines (I), cause, similarly to a commercially employed Group VIII metal complex comprising triphenylphosphine, no side reactions such as hydrogenation and isomerization, while the former has higher n/iso ratio and catalytic activity than the latter.

In the hydroformylation of 1-octene, comparison of Examples 8 and 9 with Comparative Examples 5 and 6 reveals that Group VIII metal complexes (A) comprising bisphosphines (I) can exert higher catalytic activity than Group VIII metal complexes comprising known bisphosphines and, further, suppress side reactions such as hydrogenation and isomerization. On the other hand, comparison of Examples 8 and 9 with Comparative Example 4 reveals that Group VIII metal complexes (A) comprising bisphosphines (I) can suppress side reactions such as hydrogenation and isomerization to a lower level and achieve higher n/iso ratio and catalytic activity than a Group VIII metal complex comprising a commercially employed triphenylphosphine.

INDUSTRIAL APPLICABILITY

According to the present invention, there are provided hydroformylation catalysts comprising Group VIII metal complex (A) that can, on hydroformylation of ethylenically unsaturated compounds, exert high catalytic activity and yield n-aldehydes with high selectivity while suppressing side reactions such as hydrogenation and isomerization, and bisphosphines (I) constituting such complexes and process for production thereof.

According to the present invention, use of the Group VIII metal complexes (A) for hydroformylation of ethylenically unsaturated compounds with carbon monoxide and hydrogen can lead to production of the corresponding n-aldehydes at high reaction rate and with high selectivity, while suppressing side reactions such as hydrogenation and isomerization.

What is claimed is:

1. A bisphosphine which is 2,2'-bis(diphenylphosphinomethyl)diphenyl ether, 2,2'-bis(diphenylphosphinomethyl)-6-methoxy-diphenyl ether, or 2,2'-bis(diphenylphosphinomethyl)-4-t-butyl-diphenyl ether.

2. A process for producing a bisphosphine of claim 1,

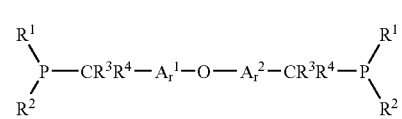

which comprises:
subjecting a compound represented by formula (II)

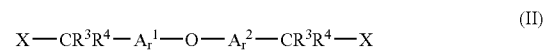

wherein $Ar^1$ and $Ar^2$ each represents a phenylene group and each together are optionally substituted by 6-methoxy or optionally by 4-t-butyl, $R^3$ and $R^4$ each represents a hydrogen atam, and X represents an arylsulfonyloxy group, alkylsulfonyloxy group or a halogen atom to phosphorylation with an alkali metal phosphide represented by formula (III)

wherein $R^1$ and $R^2$ are each phenyl and M represents lithium atom, a sodium atom or potassium atom.

3. The process according to claim 2, wherein said phosphorization is carried out in the presence of an ether-based solvent.

4. The process according to claim 3, wherein said ether-based solvent is selected from the group consisting of 1,4-dioxane, dibutyl ether, 2-ethoxyethyl ether, diethyleneglycol dimethyl ether, tetrahydrofuran and diethyl ether.

5. The process according to claim 3, wherein said solvent comprises a mixed solvent comprising tetrahydrofuran and dibutyl ether.

6. The process according to claim 2, wherein said alkali metal phosphide is used in an amount ranging from 2 to 4 moles per mole of said compound represented by the general formula (II).

7. The process according to claim 6, wherein said alkali metal phosphide is used in an amount ranging from 2 to 2.2 moles per mole of said compound represented by the general formula (II).

8. A Group VIII metal complex, comprising:
a bisphosphine of claim 1

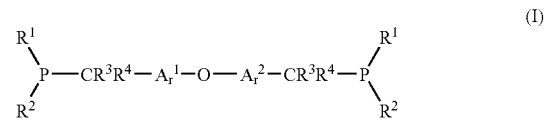

and a Group VIII metal compound.

9. The Group VIII metal complex according to claim 8, wherein said Group VIII metal compound is a rhodium compound, cobalt compound, ruthenium compound or iron compound having catalytic activity for hydroformylation.

10. The Group VIII metal complex according to claim 9, wherein said Group VIII metal compound is a rhodium compound selected from the group consisting of RhO, $RhO_2$, $Rh_2O$, $Rh_2O_3$, rhodium nitrate, rhodium sulfate, rhodium chloride, rhodium iodide, rhodium acetate, $Rh(acac)(CO)_2$, $RhCl(CO)(PPh_3)_2$, $RhCl(CO)(AsPh_3)_2$, $RhCl(PPh_3)_3$, $RhBr(CO)(PPh_3)_2$, $RH_4(CO)_{12}$ and $Rh_6(CO)_{16}$.

11. The Group VIII metal complex according to claim 10, wherein said Group VIII metal compound is $Rh(acac)(CO)_2$.

12. The Group VIII metal complex according to claim 8, wherein the amount of said bisphosphine used is in a range of 2 to 10000 moles in terms of phosphorus atom per mole of said Group VIII metal compound in terms of Group VIII metal atom.

13. The Group VIII metal complex according to claim 12, wherein the amount of said bisphosphine used is in a range of 2 to 1000 moles in terms of phosphorus atom per mole of said Group VIII metal compound in terms of Group VIII metal atom.

14. A process for producing aldehydes, which comprises: hydroformylating ethylenically unsaturated compounds with carbon monoxide and hydrogen in the presence of a catalyst of a Group VIII metal complex as defined in claim 8 to produce the corresponding aldehydes.

15. The process according to claim 14, wherein a mixed gas comprising carbon monoxide and hydrogen having a $H_2/CO$ molar ratio of 0.1 to 10 is fed into the reaction.

16. The process according to claim 15, wherein a said mixed gas comprising carbon monoxide and hydrogen has a $H_2/CO$ molar ratio of 0.5 to 2.

17. The process according to claim 14, wherein the reaction pressure is in a range of 0.1 to 10 Mpa.

18. The process according to claim 17, wherein the reaction pressure is in a range of 0.2 to 5 Mpa.

19. The process according to claim 14, wherein the reaction temperature is in a range of 40 to 150° C.

20. The process according to claim 19, wherein the reaction temperature is in a range of 60 to 130° C.

21. The process according to claim 14, wherein the amount of said Group VIII metal complex is in a range of 0.0001 to 1000 milligram-atom in terms of the Group VIII metal atom per liter of the reaction liquid.

22. The process according to claim 21, wherein the amount of said Group VIII metal complex is in a range of 0.005 to 10 milligram-atom in terms of the Group VIII metal atom per liter of the reaction liquid.

* * * * *